US00PP19376P2

(12) United States Plant Patent
Tristram

(10) Patent No.: US PP19,376 P2
(45) Date of Patent: Oct. 21, 2008

(54) ***GAURA* PLANT NAMED 'WALSNOFOU'**

(50) Latin Name: *Gaura lindheimeri*
Varietal Denomination: Walsnofou

(76) Inventor: David Tristram, Walberton Nursery, Yapton Lane, Walberton, Arundel, West Sussex BN18 0AS (GB)

( * ) Notice: Subject to any disclaimer, the term of this patent is extended or adjusted under 35 U.S.C. 154(b) by 0 days.

(21) Appl. No.: 11/732,222

(22) Filed: Apr. 2, 2007

(51) Int. Cl.
*A01H 5/00* (2006.01)

(52) U.S. Cl. ..... Plt./432

(58) Field of Classification Search ..... Plt./432
See application file for complete search history.

*Primary Examiner*—Kent L Bell
*Assistant Examiner*—Georgia Helmer

(57) ABSTRACT

A new cultivar of *Gaura* plant named 'WALSNOFOU' that is characterized by dense upright habit throughout season, stiff well-branched stems, white flowers, and medium-green foliage. In combination these traits set 'WALSNOFOU' apart from all other existing varieties of *Gaura* known to the inventor.

2 Drawing Sheets

Genus: *Gaura*.
Species: *lindheimeri*.
Denomination: 'WALSNOFOU'.

BACKGROUND OF THE INVENTION

The present invention relates to a new and distinct variety of butterfly bush grown for use as an ornamental plant for herbaceous borders and the landscape. The new cultivar is known botanically as *Gaura lindheimeri* and will be referred to hereinafter by the cultivar name 'WALSNOFOU'.

In 1984, the inventor began a *Gaura* breeding program with the intention of developing new varieties with sturdier plant habit and dense floriferous blooming. The inventor has already raised and introduced a pink-flowered *Gaura* with these attributes, namely *Gaura* 'WALGAUPF' (U.S. Plant Pat. No. 15,555). The goal of the present invention has been to achieve a similar result in a pure white flowered form.

The inventor's initial material was obtained as commercially available seed of the species *Gaura lindheimeri*. The inventor raised seedlings in an unheated greenhouse and grew on the plants to maturity in containers in an outdoor nursery production area in Arundel, West Sussex, United Kingdom. The plants were allowed to remain outdoors all year round so that overall plant and flowering habits could be evaluated and compared after a full growing season.

In 1997, the inventor observed in that year's set of flowering plants an individual *Gaura* plant which exhibited distinctly stiffer stems in comparison with all of the other seedlings of similar age. From this plant, the inventor collected self-pollinated seed, and sowed this seed with the intention of re-selecting for the same desirable characteristics. The resulting seedlings were observed for two or more years, and in 2000 the inventor determined that one particular plant, 'WALSNOFOU' was overall the most attractive and distinct from all forms of the species previously known or raised by the inventor.

The distinguishing characteristics of 'WALSNOFOU' are stiff well-branched stems which bear white flowers in profusion, and whose overall plant habit remains dense and upright throughout the season. In these respects, 'WALSNOFOU' is markedly different from the antecedent plants of the species *Gaura lindheimeri* which the inventor had raised. Such seed-raised plants were typically loose and open in habit and in their flowering.

The dimensions of 'WALSNOFOU' at maturity are 80 cm. in height and 60 cm. in width. Cultural requirements are well-draining soil, and full sun, with infrequent to moderate water. 'WALSNOFOU' is hardy in USDA Zones 5–10.

The first asexual propagation was conducted by the inventor in 2003. Propagation was carried out by the inventor in unheated greenhouses at the inventor's nursery in Arundel, United Kingdom using the method of stem cuttings. The differentiating characteristics of 'WALSNOFOU' are determined stable and reproduce true to type during successive generations of asexual reproduction.

SUMMARY OF THE INVENTION

The following traits have been repeatedly observed and represent the distinguishing characteristics of the new *Gaura* cultivar 'WALSNOFOU'. In combination these traits set 'WALSNOFOU' apart from all other *Gaura* known to the inventor. 'WALSNOFOU' has not been tested under all possible conditions and phenotypic differences may be observed with variations in environmental, climatic and cultural conditions, however, without any variance in genotype.

1. 'WALSNOFOU' exhibits dense upright habit.
2. 'WALSNOFOU' retains habit through the season.
3. 'WALSNOFOU' exhibits freely borne white flowers.
4. 'WALSNOFOU' exhibits stiff, well-branched stems.
5. 'WALSNOFOU' exhibits medium-green foliage.
6. 'WALSNOFOU' is asexually propagated using the method of stem cuttings.
7. 'WALSNOFOU' is hardy in USDA Zones 5–10.
8. 'WALSNOFOU' reaches 80 cm in height and 60 cm in width at maturity.

BRIEF DESCRIPTION OF THE DRAWINGS

The accompanying color drawings illustrate the overall appearance of the new *Gaura* cultivar named 'WALSNOFOU' showing color as true as is reasonably possible to obtain in color reproductions of this type. Color in the drawings may differ from color values cited in the detailed botanical description, which accurately describe the actual color of the new variety 'WALSNOFOU'.

The drawing labeled

The drawing labeled

Figure 1:
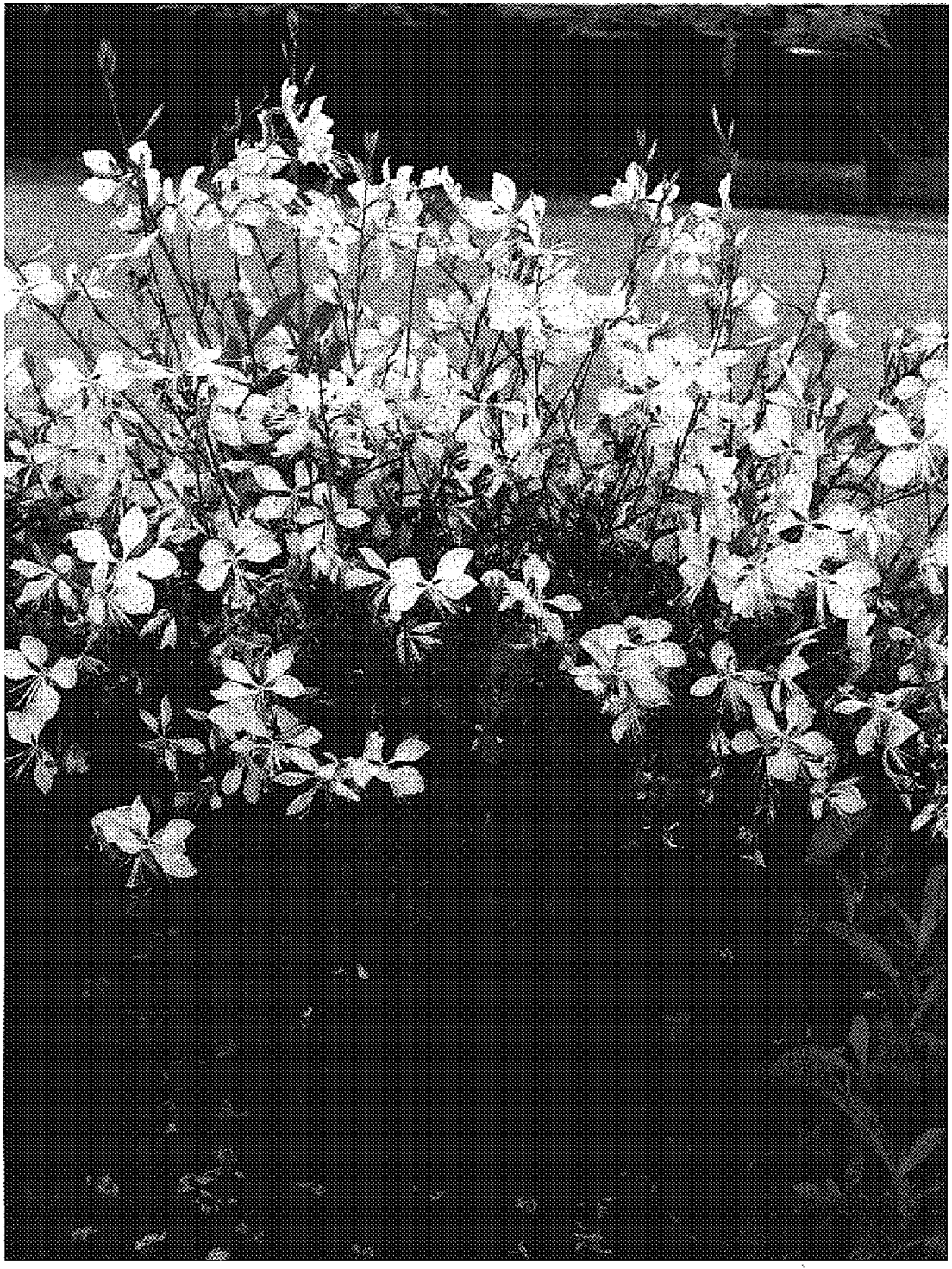
FIG. 1 depicts an individual plant of 'WALSNOFOU' in full bloom. The illustrated plant is two years old and is growing in a 3 liter pot out of doors at the inventor's nursery in Arundel, West Sussex, United Kingdom. No growth regulators have been used.
Figure 2:
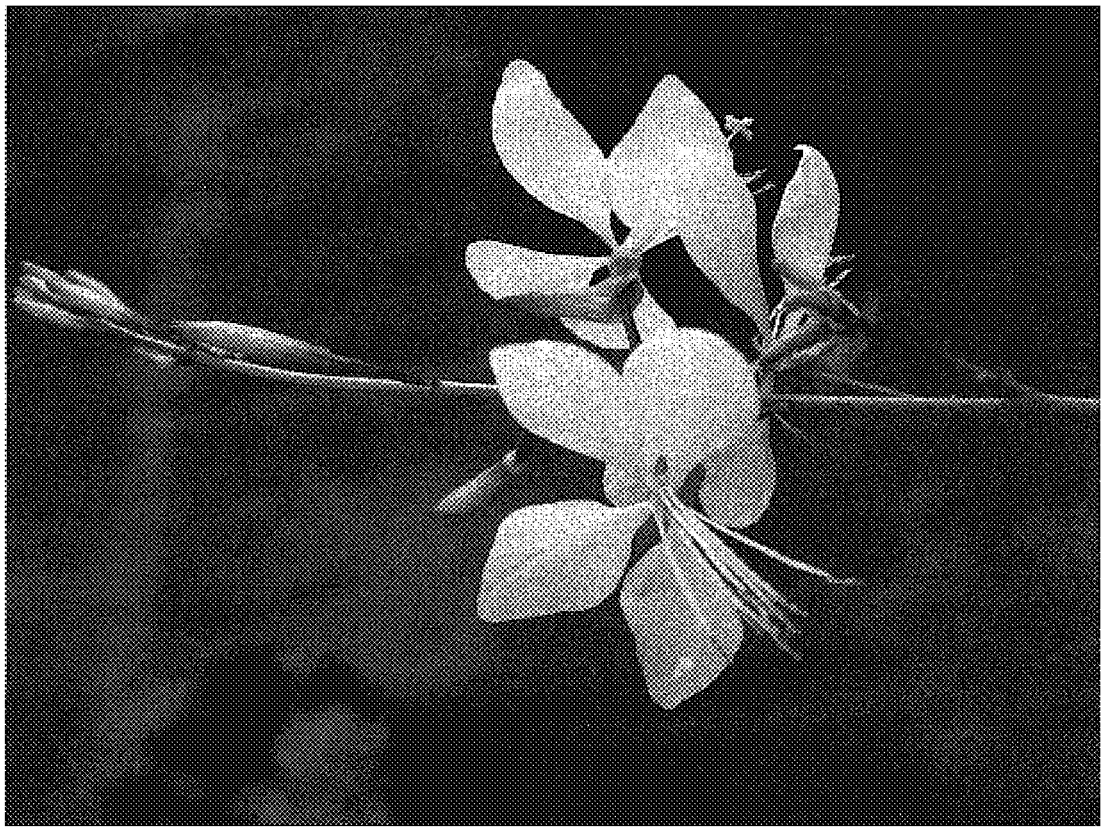
FIG. 2 depicts a close-up view of the flowers of the same plant utilized for FIG. 1.

Colors in the drawings may appear different from actual color due to light reflectance, but as close as is reasonably possible to obtain by conventional photography.

BOTANICAL DESCRIPTION OF THE PLANT

The following is a detailed botanical description of the new *Gaura* variety named 'WALSNOFOU'. Data was collected in Arroyo Grande, Calif. from 12-month-old plants that were grown in 2-liter containers out-of-doors in full sun. The color determinations are in accordance with the 2001 Royal Horticultural Society Colour Chart of London, England, except where general color terms of ordinary dictionary significance are used. The growing requirements are similar to other *Gaura*.

Botanical classification: *Gaura lindheimeri* 'WALSNOFOU'.
Family: Onagraceae.
Genus: *Gaura*.
species: *lindheimeri*.
Denomination: 'WALSNOFOU'.
Common name: Butterfly bush.
Commercial classification: Perennial.
Use: Ornamental plant for herbaceous borders and the landscape.
Cultural requirements: Plant in well-draining soil, and full sun, with infrequent to moderate water.
Susceptibility to pests and disease: None known to the inventor.
Root system: Deep rooting contributes to drought tolerance.
Parentage: 'WALSNOFOU' is a selected seedling which was raised from seed which was collected from a self-fertilized unnamed and unreleased seed-raised plant of *Gaura lindheimeri*.
Plant description:
- *Bloom period.*—Late spring through summer.
- *Habit.*—Dense upright habit.
- *Dimensions* (*first year*).—80 cm in height and 30 cm in width.
- *Dimensions* (*at maturity*).—80 cm in height and 60 cm in width.
- *Hardiness.*—USDA Zones 5–10.
- *Propagation.*—Propagation is accomplished using the method of stem cuttings.
- *Time to develop roots.*—2–3 weeks from initial cutting.
- *Crop time.*—4–6 months to produce a finished 1-liter container.

Stem:
- *Shape.*—Cylindrical.
- *Color.*—Emerges 138B becoming 182B at maturity.
- *Texture.*—Stiff.
- *Dimensions.*—12 cm. in length and 3 mm. in diameter.
- *Surface.*—Pubescent.
- *Internode length* (*average*).—0.50 cm.

Foliage:
- *Type.*—Basal and cauline.
- *Shape.*—Oblanceolate.
- *Division.*—Simple.
- *Apex.*—Acute.
- *Base.*—Attenuate.
- *Venation pattern.*—Pinnate.
- *Vein color* (*adaxial surface*).—191D.
- *Vein color* (*abaxial surface*).—191D.
- *Margins.*—Entire.
- *Attachment.*—Sub-sessile.
- *Arrangement.*—Alternate.
- *Leaf surface* (*adaxial*).—Puberulent.
- *Leaf surface* (*abaxial*).—Puberulent.
- *Leaf appearance.*—Matte.
- *Leaf length* (*average*).—5 cm.
- *Leaf width* (*average*).—1 cm.
- *Leaf color* (*adaxial surface*).—138A.
- *Leaf color* (*abaxial surface*).—138B.
- *Fragrance.*—None observed.

Flowers:
- *Inflorescence.*—Raceme.
- *Flower quantity per inflorescence* (*range*).—10–25.
- *Flower quantity per plant* (*range*).—100–300.
- *Lastingness of flower* (*average*).—24 hours.
- *Flower depth.*—4 cm.
- *Flower diameter.*—3.75 cm.
- *Flower color.*—155B.
- *Flower shape.*—Clawed opening flat.
- *Flowers persistent or self-cleaning.*—Self-cleaning.
- *Aspect.*—Facing outward and upward.
- *Bud dimensions.*—1.75 cm in length and 0.40 cm in width.
- *Bud quantity.*—10–25 buds per inflorescence.
- *Bud shape.*—Linear.
- *Bud color.*—Mostly 160C; 178A towards base.
- *Bud surface.*—Pubescent.
- *Bud apex.*—Acute.
- *Bud base.*—Truncate.
- *Petals.*—Four in number.
- *Petal shape.*—Obovate.
- *Petal color* (*adaxial and abaxial surface*).—155B.
- *Petal dimensions.*—2 cm in length and 1 cm in width.
- *Petals fused or unfused.*—Unfused.
- *Petal margin.*—Entire.
- *Petal apex.*—Broadly acute.
- *Petal base.*—Attenuated.
- *Petal surfaces* (*adaxial and abaxial*).—Glabrous.
- *Calyx.*—Petaloid.
- *Sepals.*—4 connate.
- *Sepals fused or unfused.*—Fused.
- *Sepal color.*—181C.
- *Sepal dimensions.*—1.75 cm in length and 0.10 cm in width.
- *Sepal surface.*—Puberulent.
- *Pedicel dimensions.*—0.50 cm in length and 1.50 mm in width.
- *Pedicel color.*—146D initially, quickly becoming 178A.
- *Pedicel shape.*—Cylindrical.
- *Pedicel surface.*—Glabrous.
- *Peduncle dimensions* (*average*).—30 cm in length and 2.50 mm in diameter.
- *Peduncle shape.*—Cylindrical.
- *Peduncle color.*—144A.
- *Peduncle surface.*—Glabrous.
- *Flower fragrance.*—None observed.

Reproductive organs:

*Stamens.*—Eight in number.
*Stamen color.*—155B.
*Stamen length* (*average*).—2.10 cm.
*Anther length.*—3 mm.
*Anther color.*—162B becoming 181D after pollen loss.
*Pollen color.*—162B.
*Pollen quantity.*—Moderate.
*Pistil.*—One in number.
*Pistil length.*—2 cm.
*Pistil color.*—155B.
*Pistil shape.*—Filament.
*Stigma shape.*—4-lobed.
*Stigma color.*—160C.
*Stigma width.*—3 mm.
*Ovary position.*—Inferior.
*Ovary color.*—138D.
*Ovary shape.*—Ovoid.
*Ovary dimensions.*—3 mm in height and 2 mm in width.

Seed production: No seed observed to date.

What is claimed is:

1. A new and distinct cultivar of *Gaura* plant named 'WALSNOFOU' as described and illustrated herein.

* * * * *